United States Patent [19]

Garrison et al.

[11] 4,087,273

[45] May 2, 1978

[54] THIOCARBAMATE-BASED SUSTAINED RELEASE HERBICIDES

[75] Inventors: Charles Michael Garrison, Fairfield; Roy Clark Mast, Cincinnati; Medford Dwight Robbins, Okeana, all of Ohio

[73] Assignee: The Procter & Gamble Company, Cincinnati, Ohio

[21] Appl. No.: 718,634

[22] Filed: Aug. 30, 1976

Related U.S. Application Data

[63] Continuation-in-part of Ser. No. 586,458, Jun. 12, 1975, abandoned.

[51] Int. Cl.$^2$ ............................................. A01N 9/12
[52] U.S. Cl. ................................. 71/100; 71/DIG. 1
[58] Field of Search ............................ 71/DIG. 1, 100

[56] References Cited

U.S. PATENT DOCUMENTS

| | | |
|---|---|---|
| 3,212,967 | 10/1965 | McFadden et al. ............. 71/DIG. 1 |
| 3,343,941 | 9/1967 | Baltazzi ............................ 71/DIG. 1 |
| 3,365,288 | 1/1968 | Detmer et al. ......................... 71/64 F |
| 3,417,181 | 12/1968 | Cardarelli ................................. 71/67 |
| 3,590,119 | 6/1971 | Cardarelli et al. ....................... 424/22 |
| 3,639,306 | 2/1972 | Sternberg et al. ..................... 428/407 |
| 3,639,583 | 2/1972 | Cardarelli et al. .................... 424/124 |
| 3,725,031 | 4/1973 | Balassa .................................. 71/115 X |
| 3,755,064 | 8/1973 | Maierson ............................ 71/DIG. 1 |
| 3,846,404 | 11/1974 | Nichols .............................. 71/DIG. 1 |
| 3,929,453 | 12/1975 | Dimitri et al. ...................... 71/100 X |

OTHER PUBLICATIONS

Cardarelli, A.C.S. Symposia, Washington, D. C., 1971, Summary and p. 11, Slow Release of Pesticides from Elastomeric Matrices.
Stokes, et al., J. Agr. Food Chem. 21, 103, (1973), abstract.
German Offen., 1,936,748 (abstract), 1-29-70.
Fr. Demande, 2,077,679 (abstract), 10-12-71.
Neogi, (1970), Polymer Selection for Controlled Release Pesticides, University of Wash. dissertation.
Fr. 1,604,868 (abstract), 1972.
Fr. Demande, 2,117,769 (abstract), 1-9-72.
Roberts, (1974), Prin. and Practice of Controlled Release Insecticide–Polymer Blends, University of Wash. dissertation.
Neogi, (1970), Polymer Selection for Controlled Release Pesticides, University of Wash. dissertation.
Roberts, (1974), Prin. and Practice of Controlled Release Insecticide–Polymer Blends, University of Wash. dissertation.

Primary Examiner—Joseph Paul Brust
Attorney, Agent, or Firm—Jerry J. Yetter; Julius P. Filcik; Richard C. Witte

[57] ABSTRACT

Particulate compositions comprising a thiocarbamate herbicide releasably contained with certain polymer matrices are herbicidally effective throughout the growing season.

5 Claims, No Drawings

THIOCARBAMATE-BASED SUSTAINED RELEASE HERBICIDES

CROSS-REFERENCE TO RELATED APPLICATION

This application is a continuation-in-part of application Ser. No. 586,458, filed June 12, 1975 and now abandoned.

BACKGROUND OF THE INVENTION

The present invention relates to sustained release herbicides. More specifically, thiocarbamate-based pre-emergence herbicides are contained within substantially dry, solid polymer matrices. The matrices are selected from substituted cellulosic and/or polypropylene materials which allow slow diffusion release of the herbicides, i.e., over a period of about four months. Accordingly, the compositions herein are herbicidally effective during this period and are specifically designed to provide a herbicidal effect throughout an average 3½ to 4 month growing season.

Much effort has been expended to provide herbicidal compositions which are effective throughout a growing season, and it would be difficult to overstate the economic value of a truly effective, season-long, sustained release herbicide. For example, the user of such a product would not have to cultivate crops throughout the entire growing season. The savings in time and labor would be substantial. Moreover, crops could be planted in narrower rows since cultivator machinery would not have to be used during the growing season. This would allow more productive use of the land.

Herbicidal chemicals are, of course, designed to prevent the germination and/or growth of weeds and weed seedlings. However, at high application rates herbicides also tend to destroy desirable crops. Accordingly, it is not possible to apply common herbicides at the extremely high levels which are required to provide season-long weed control without damaging crops. Repeated applications of herbicides at weed-controlling levels (which are safe for crops) throughout the growing season is one method of crop cultivation. A more desirable method would be to use sustained release compositions which provide a metered dose of herbicide at or somewhat above its minimum effective level throughout the season.

As is well recognized in the agricultural arts, good, sustained release, season-long herbicides have not been available heretofore. In particular, no good season-long herbicide has been available for use on soybeans and like crops.

The present invention employs thiocarbamate-based pre-emergence herbicides which are safe for use on crops such as soybeans. The herbicides are contained within a polymer matrix which is specially selected to release the herbicide at an extremely slow rate, thereby providing season-long weed control.

Surprisingly, it has been discovered that many common pre-emergence herbicides are not suitable for use in the practice of this invention. Moreover, many common polymers are not useful herein. However, the particular combinations of thiocarbamate-based herbicides and selected polymer carrier matrices disclosed herein do meet the requirements for season-long weed control.

RELATED REFERENCES

The following references relate to sustained release carriers for agricultural compositions, and the like.

U.S. Pat. No. 3,846,404, Nichols, 1974, discloses cellulose acetates which can be used as carriers for liquids or solutions of solids.

U.S. Pat. Nos. 3,417,181 (1968); 3,639,583 (1967); and 3,590,119 (1970), each to Cardarelli, relate to slow release of biologically active agents from polymer matrices. See also, Cardarelli, N. F. *SLOW RELEASE OF PESTICIDE FROM ELASTOMERIC MATRICES*, A. C. S. Symposia, Washington. D.C.

U.S. Pat. No. 3,365,288, 1968, to Detmer, describes a coated fertilizer particle with controlled release.

U.S. Pat. No. 3,639,306, 1972, to Sternberg, discloses polymeric particles which consist of a microporous or diffusive barrier in a substantially hollow interior containing a material which escapes from the particle by diffusion.

U.S. Pat. No. 3,755,064, 1973, to Majerson, describes encapsulated components contained within a three-dimensional, water-insoluble, polymeric web.

German Offen, Pat. No. 1,936,748, 1970, to Ciba-Geigy A. G. describes polymeric granules having pesticides adsorbed on the surface. The granules are characterized by specific inner surface areas and average diameters of 400 Angstroms.

French Demande Pat. No. 2,077,679, 1971 to Boullenger, describes plastic plates of an organophosphate pesticide and "coevaporator".

French Pat. No. 1,604,868, 1972, to Dynachim S.a.r.l. discloses the formation of a plastic product containing a volatile pesticide and asbestos fiber. See also French Demande Pat. No. 2,117,769, 1972, to Dynachim, for a slow release phosphate pesticide impregnated in a polymeric matrix.

In addition to the foregoing reference, Stokes, R. A., et al., J. Agr. Food Chem. 21, 103 (1973) describe the use of granular formulations of aldicarb and dimethoate insecticides prepared using cellulose acetate, polyamide, polyester, polyvinylchloride, polyurethane and urea-formaldehyde polymer matrices. Charcoal was added to some of the compositions. These compositions are said to release the insecticide more slowly than standard corn cob formulations.

S. Neogi, *POLYMER SELECTION FOR CONTROLLED RELEASE PESTICIDES*, University of Washington, Ph.D. dissertation, University Microfilms (1970) describes the factors which influence the rate of diffusion of pesticides from polymeric matrices, such as polyamides.

S. Roberts, *PRINCIPLES AND PRACTICE OF CONTROLLED RELEASE INSECTICIDE-POLYMER BLENDS*, University of Washington, Ph.D. dissertation, University Microfilm (1974) expands and extends the Neogi work, above, and includes field test data or prolonged release of carbofuran insecticide in soil to protect tree seedlings from insect attack.

SUMMARY OF THE INVENTION

The present invention encompasses a sustained release composition comprising an effective amount of a thiocarbamate-based pre-emergence herbicide which exists as a solid solution or dispersion in an otherwise substantially dry, solid, water-insoluble polymer matrix (said polymer being defined more fully hereinafter), said composition being characterized by an effective diffusion coefficient of the herbicide from the polymer matrix in the range from about $10^{-10}$ cm$^2$/sec. to about $10^{-12}$ cm$^2$/sec.

The present invention also encompasses a process for preparing a sustained release herbicidal composition, comprising heating a polymer selected from the group consisting of water-insoluble acylated cellulose derivatives and polypropylene, and a thiocarbamate-based pre-emergence herbicide (especially those suitable for use with soybeans) to provide a homogeneous, substantially anhydrous mixture (usually a "melt"), said mixture comprising substantially unpolymerized or undecomposed herbicide, and cooling the mixture at a rate whereby the polymer solidifies to a substantially solid form containing the herbicide.

The present invention are encompasses a process for controlling undesirable vegetation, especially in the presence of soybeans, comprising applying to the soil containing the seeds of said undesirable vegetation prior to, or at the time of, germination, a composition prepared according to this invention.

DETAILED DESCRIPTION OF THE INVENTION

The present compositions and processes employ commercially available materials which are described more fully hereinafter. All percentages are by weight.

Polymer Matrix

The polymeric material used to prepare the carrier matrix of the present compositions is selected from water-insoluble acylated cellulose derivatives and polypropylene. Surprisingly, many commercial polymers such as the methacrylates perform poorly, or not at all, when used as polymer matrices in the manner of the present invention.

The acylated cellulose derivatives used herein are the materials well known in the art. Acylated cellulosics such as cellulose propionate, cellulose butyrate, and the like, are all useful herein, but "mixed" cellulosics such as cellulose acetate-butyrate, cellulose acetatepropionate, cellulose propionate-butyrate, and the like, are especially good for this purpose. Cellulose acetate, itself, performs poorly and is not contemplated for use in the present invention.

The acylated cellulose derivatives are commercially available or can be prepared in well-known fashion. For example, cellulose acetate can be prepared by acetylating a cellulose feedstock using glacial acetic acid, sulfuric acid and acetic anhydride. The resulting cellulose acetate is the acetone-soluble, water-insoluble, thermoplastic material which is commercially available from a variety of sources, and can be used to prepare the "mixed" cellulosics mentioned above.

The higher (i.e., acyl groups longer than acetate) acylated cellulosics can be prepared in like manner, for example using propionic acid, butyric acid, and the like.

The so-called "mixed" cellulose derivatives can be prepared, for example, by partially acetylating cellulose and thereafter reacting the acetylated cellulose with a C$_3$, or higher, carboxylic acid or acid anhydride.

As noted above, the acylated cellulose derivatives employed herein are the substantially water-insoluble thermoplastic materials well known in the art. These materials are characterized by a degree of acylation in the range from about 1 to about 3 (3 being the theoretical maximum degree of acylation).

Typical acylated cellulosics herein include cellulose propionate characterized by a degree of propylation in the range from about 1 to about 3, especially 1.5 to about 2.6, and mixed acetyl-higher acyl cellulosics, especially acetylated cellulose characterized by a degree of acetylation in the range from about 1.8 to about 2.7 and containing from about 10% to about 35%, more preferably 15% to 25%, by weight of butyrate substituents. This latter material is preferred for use herein.

A more complete description of cellulosics of the foregoing type which are useful in the practice of this invention is contained in the technical publication, AN INTRODUCTION TO EASTMAN® CELLULOSE ESTERS, available from Eastman Chemical Products, Inc., Kingsport, Tennessee 37,662, the disclosures of which are incorporated herein by reference.

In particular, the Eastman ® cellulose acetate-butyrates designated 381–0.1; 381–0.5; 381–2; 381–20; 272–3; 272–20; 171–2; 171–15; 171–25; and 171–40 are excellent for use in the present compositions. Thiocarbamates, especially S-propyl dipropylthiocarbamate, used with cellulose acetate butyrate having 17% or 27% butyryl content yields controlled released herbicide compositions which are exceptionally preferred.

Cellulose acetate propionate, EASTMAN ®, designated 482–0.5 and 482–20 are also desirable for use herein.

Other commercially available mixed cellulose derivatives useful herein are available from Aldrich as cellulose propionate (designated 18,097–1) and Aldrich cellulose acetate butyrate with 17% butyryl content (designated 18,096–3).

Polypropylene is another type of matrix material useful herein. Thermoplastic polypropylene having a flow point below the decomposition/polymerization temperature of the thiocarbamate herbicides is used herein, and this polypropylene material is available from various commercial sources (e.g., Rexene Polymers Co.).

Herbicide

The herbicide materials employed in the practice of this invention are thiocarbamate materials of the formula

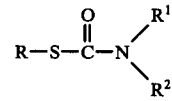

wherein R, R$^1$ and R$^2$ are alkyl (preferred), aryl or substituted alkyl or aryl groups, and wherein groups R, R$^1$ and R$^2$ can each be the same or different. Listings of thiocarbamate-based pre-emergence herbicides appear in standard texts; see U.S.D.A. *SUMMARY OF REGISTERED AGRICULTURAL PESTICIDE CHEMICAL USES,* 3rd Ed., issued August 31, 1968, incorporated herein by reference. Many such materials are available commercially.

With reference to the foregoing formula, typical examples of thiocarbamate herbicides useful herein are compounds wherein R is methyl, ethyl, propyl, butyl, or 2,3-dichloroallyl; wherein R$^1$ can be methyl, ethyl, cyclohexyl, isobutyl, propyl, or isopropyl; and wherein R$^2$ can be ethyl, propyl, isopropyl, butyl and isobutyl. Compounds wherein the substituted groups are aryl, e.g., naphthyl or phenyl, can be used.

Specific examples of thiocarbamate herbicides herein include S-propyl dipropylthiocarbamate (VERNAM: preferred herein); S-propyl ethylbutylthiocarbamate (TILLAM); S-ethyl cyclohexylethylthiocarbamate; S-ethyl diisobutylthiocarbamate; S-ethyl dipropylthiocarbamate; and S-2,3-dichloroallyl diisopropylthiocarbamate.

Fillers

The compositions herein can optionally contain filler materials. The fillers employed herein sometimes additionally slow the diffusion of the herbicide through the polymer matrix. Moreover, appropriately chosen fillers aid in processing and make mixing/handling easier. Perhaps most importantly, the fillers serve to sorb fluid parts of the polymer matrices caused by the presence of lower molecular weight polymers present in commercial polymer mixtures. By sorbing these fluid regions, more uniform diffusion is secured. The fillers, which can comprise from about 5% to about 15% of the total compositions herein, are various solid materials in the particle size range below about 2 microns, and generally fall within the sub-micron size range. Particularly useful filler materials herein include various clays, especially kaolin available as Hydrite UF, Georgia Kaolin Co., carbon black such as that available for use in the automotive tire industry, and high surface area activated charcoal. The carbon black and charcoals employed herein are available as sub-micron dusts.

In the preparation of the present compositions containing the fillers, the herbicide, polymer and filler are intimately admixed and handled in the manner more fully disclosed hereinafter.

Preparation

The compositions herein are prepared by intimately admixing the polymer material, the thiocarbamate herbicide and the optional filler, with heating to 150° C–225° C, to provide a homogeneous, substantially anhydrous mixture. The heated mixture is in the form of a liquid melt. The homogeneous mixture is then cooled at a rate whereby the polymer solidifies into a substantially solid form containing the herbicide.

In a typical procedure, an intimate mixture of powdered polymer thiocarbamate herbicide is heated at a temperature, and for a time, wherein substantial decomposition and/or polymerization of the herbicide does not occur, to provide a melt. An important consideration is that a homogeneous mixture be secured and that the heating temperature and time be regulated so as to avoid any undesirable reaction or undue volatilization of the herbicide. (The polymers herein are quite heat stable at temperatures well above the stability limits of the herbicides.) Appropriate temperatures can easily be selected, depending on the decomposition temperature of the particular thiocarbamate being used.

Diffusion Measurements

The compositions herein are characterized by the extremely low rate of diffusion of the thiocarbamate herbicide through the polymer matrix into the external environment where the herbicidal effect is desired. The compositions herein are characterized by an effective diffusion coefficient in the range from about $10^{-10}$ cm$^2$/sec. to about $10^{-12}$ cm$^2$/sec., thereby providing release of herbicide throughout a growing season in the desired manner. The presence of water within the polymer matrix substantially increases this rate of diffusion; any residual water is substantially removed by processing in the above manner.

When preparing compositions within the scope of this invention, the effective rate of diffusion can be established in the following manner. The selected polymer and herbicide are intimately mixed and melted to provide a homogeneous composition, taking into consideration the factors regarding heating times, temperatures, etc., described hereinabove. After the composition is secured, it is cooled to room temperature. A measured aliquot of water is added and the rate of release of herbicide into the water is measured over a period of time.

In a typical mode, a homogeneous polymer/herbicide melt is prepared in a 2 cm. diameter diffusion cell and cooled to room temperature, thereby providing a solid disk of a composition typical of this invention of ca. 0.2–0.3 cm. thickness. This disk is thereafter covered with 20–25 ml. water and gently agitated at a temperature of ca. 23° C. Periodically, samples of the water are taken and the amount of herbicide therein is determined by carbon analysis or spectrophotometric means. A plot of the proportion of herbicide diffused vs. the square root of time yields a substantially linear graph whose slope contains the effective diffusion coefficient in cm$^2$/sec. The mathematics of determining diffusion coefficients from the slope of graphs obtained in this manner are fully set forth in Crank, J., *THE MATHEMATICS OF DIFFUSION*, Clarendon Press, Oxford, 1956, p. 45, the disclosures of which are incorporated herein by reference.

Although many advances have been made in the understanding of interactions between polymers and small organic molecules such as herbicides (see especially the thesis of S. Roberts, cited above), it is not yet possible to predict which polymers will serve as satisfactory matrices for particular herbicides. It is a gross oversimplification to expect that any thermoplastic polymer can accommodate any herbicide. Satisfactory polymer-plus-herbicide compositions which contain 50% or more herbicide are even more difficult to define using known thoretical principles. As can be seen from Table 1, a wide variety of polymers are simply not useful for preparing controlled release thiocarbamate herbicide compositions in the manner of this invention.

The compositions listed in Table 1 were prepared by finely grinding the polymers, mixing the ground polymers with the specified amount of Vernam, heating the mixture until molten, and then cooling the melts to room temperature. On visual examination the respective compositions were sometimes found to be rubbery (R). Seepage (S) of Vernam was often noted. In some instances, the melt remained liquid (L) on cooling. In other instances the polymer and Vernam were immiscible (I) and did not fuse together or were non-homogeneous (NH) in the cooled state. In still other cases, the cooled melts were tacky (T), pasty (P) or moist (M) with Vernam. In all cases, the compositions were judged to be unfit for use as controlled release herbicides.

TABLE 1

| Polymer | % Vernam | Product Characteristics |
|---|---|---|
| Polyethylene (low density) | 23 | R;S |
| Polyethylene (high density) | 19 | S |
| Polystyrene | 53 | L |
| Polystyrene-acrylonitrile | 52 | S |

TABLE 1-continued

| Polymer | % Vernam | Product Characteristics |
| --- | --- | --- |
| Polyacrylonitrile-butadiene-styrene | 52 | S |
| Polyacrylonitrile | 19 | I |
| Polyacrylate | 23 | S |
| Polyethylene-vinylacetate | 52 | R;S |
| Polyurethane | 51 | W;R |
| Polycaprolactone | 50 | W |
| Polycarbonate | 52 | S |
| Polystyrene-butadiene | 53 | L |
| Polydicyclopentadiene | 27 | T |
| Poly-α-methylstyrene | 26 | P |
| Polyterpene Resin | 27 | P |
| Polymethyl-methacrylates* | 48–49 | S;M;I |
| Polybutylmethacrylate | 52 | NH |
| Phenoxy Resin | 52 | NH |
| Polyhexamethylene | 47 | S |
| Polylauryllactam | 51 | I |

*Low, medium and very high molecular weights

The following examples describe highly preferred embodiments of the instant invention. The compositions described in the examples are especially useful as broad spectrum pre-emergence herbicides in the presence of soybeans and are especially useful for controlling the following weeds: crabgrass, barnyardgrass, foxtails, johnsongrass from seedlings, nutsedge, goosegrass, wild cane, pigweed, lambsquarters, sicklepod, carpetweed, and Florida purslane.

EXAMPLE I

A herbicidal composition of the present type is prepared in the following manner. Three grams of ground (20–40 mesh) cellulose acetate-butyrate (degree of acetate substitution ca. 2.3; 17% butyrate) is mixed thoroughly with 8.4 grams of distilled, commercial, liquid Vernam. The moist paste is thereafter placed on a sheet of glass and spread to a uniform thickness of ca. 5 mm. The preparation is heated for about 8 minutes at about 220° C, whereupon a clear amber fluid is formed. After cooling to room temperature, a solid sheet of homogeneous product ca. 1 mm. thick containing 70% by weight herbicide and 30% by weight polymer is secured. The product is cut into cubes about 1 mm. on a side, and is suitable for application in that form.

It will be appreciated that the cellulose acetate butyrate employed in the composition of Example I is especially useful in preparing compositions of the present type inasmuch as it can be so heavily loaded with herbicide.

In the composition of Example I, the Vernam is replaced by an equivalent amount of S-propyl ethylbutylthiocarbamate and S-ethyl cyclohexylethylthiocarbamate, respectively, and excellent results are secured.

In the composition of Example I, the cellulose acetatebutyrate is replaced by EASTMAN® CAB's 381-0.1; 171-40; 381.20 and Aldrich cellulose propionate 18,097-1, respectively, and excellent results are secured.

EXAMPLE II

A season-long herbicide suitable for use on soybeans is prepared from 125 grams of Vernam (technical grade) and 125 grams of cellulose propionate (thermoplastic) in the following manner. 125 grams of the Vernam are heated in a 500 ml. round-bottom flask with a few beads of the cellulose propionate. After the initial few beads of cellulose propionate are dissolved, the remainder of the cellulose propionate is added slowly and portion-wise allowing each portion to dissolve prior to the next addition. The final melting temperature of the mixture is 235° C.

The homogeneous mixture prepared in the foregoing manner is poured onto a flat surface to cool, and the resulting cooled mass is powdered in a Waring blender. The powdered material is thereafter extruded from a capillary rheometer to 1 mm. diameter strands (490 psi; 88° C). The strands are thereafter cut to 1 mm. in length and stored for use.

In the composition of Example II, the cellulose propionate is replaced by an equivalent amount of cellulose butyrate and equivalent results are secured.

EXAMPLE III

A mixture of 200 grams of distilled N,N-dipropyl-S-propyl thiocarbamate and 200 g. of polypropylene beads (Rexene Polymer Company, Type YPE31-S-3, melt flow rate 3 g./10 min. at 230° C) is placed in a 1,000 ml. resin flask. A condenser and stirring shaft with bearing are inserted into the 3-neck flask head and the assembly is sealed. The flask is placed in a 210° C. oil bath and the contents are stirred. After the contents become molten (ca. 30 minutes), the resin flask is removed from the oil bath. The contents are then removed, allowed to cool, and cut into pieces about 8 mm. wide. Cutting is facilitated by flattening the molten mixture into sheets prior to cooling.

The pieces of composition prepared in the foregoing manner are fed batch-wise into a 25 cc. capillary rheometer preheated to 150° C. The composition is extruded through a 1 mm. diameter die head using ca. 400 psi pressure. The strands of composition prepared in this manner are suitable for cutting into any desired length for use as a season-long herbicide.

In the composition of Example III, the N,N-dipropyl-S-propylthiocarbamate is replaced by an equivalent amount of S-ethyl phenylpropylthiocarbamate and S-pentyl dipentylthiocarbamate to provide controlled release compositions.

Usage

Compositions prepared in the manner of the foregoing examples are designed for application prior to, or at the time of, weed seed germination, or shortly thereafter. The compositions are spread onto the soil to be treated and covered with a thin layer of earth. The compositions remain in place and provide an effective amount of herbicide to the damp earth over a period of 3½ to 4 months.

It will be appreciated that the particulate compositions herein should be uniformly spread over the soil being treated. Moreover, it will be recognized by those skilled in the art that the herbicides used herein will diffuse only a short distance from the particles, and are effective only over that distance. Accordingly, small particles of the compositions herein are used to provide uniform, close coverage of the treated soil. Conversely, extremely fine particles of herbicide/polymer compositions do not provide sufficiently slow diffusion to achieve season-long weed control.

Calculations indicate that uniform coverage with ca. $10^7$ particles/acre yields a particle separation distance of ca. 2–3 cm. This is sufficient to provide good weed control.

In addition to the foregoing considerations, the "load" of herbicide per particle and the average application rate (ca. 1–20 lbs) of active herbicide per acre must be considered when selecting optimal particle sizes for the compositions herein.

In general terms, the lower the diffusion coefficient the smaller the particle that can be used, at a given loading in the range of ca. 25% to 50% by weight of herbicide. Typical loads, application rates and particle sizes for the compositions herein containing Vernam appear in Table 2. (The particle size relates to the smallest dimension of the particle.)

TABLE 2

| Effective Diffusion Coefficient* | Size (mm.)** | % Load | Application Rate*** |
|---|---|---|---|
| $10^{-10}$ | 1 | 40 | 4 |
| | 1 | 50 | 6 |
| $10^{-11}$ | 1 | 25 | 4 |
| | 0.8 | 50 | 4 |
| | 1 | 40 | 6 |
| $10^{-12}$ | 0.8 | 25 | 4 |
| | 1 | 25 | 6 |
| | 0.5 | 50 | 6 |
| $10^{-13}$ | 0.5 | 40 | 4 |
| | 0.5 | 50 | 6 |

*As determined herein.
**Based on particle separations of 2–3 cm. giving on the order of $10^7$ particles/acre.
***Application rates are based on herbicide active (lbs./acre for Vernam).

As can be seen from the foregoing, effective sustained release herbicide compositions comprising an effective (weed-controlling) amount of a thiocarbamate-based preemergence herbicide which exists as a solid solution or dispersion in an otherwise substantially dry, solid, water-insoluble polymer matrix which is a member selected from the group consisting of thermoplastic $C_3$ and higher acylated cellulosics, mixed acylated cellulosics and thermoplastic polypropylene are provided by this invention.

Preferred compositions herein are characterized by: a herbicide load in the range of ca. 25% to 70% by weight; a particle whose smallest dimension is 0.5 mm to 1 mm; and an effective diffusion coefficient of $10^{-10}$ to $10^{-12}$ cm$^2$/sec. Such particles are applied at a rate whereby ca. 1 to 20, preferably 1 to 10, lbs. of herbicide/acre are provided.

It will be appreciated that the highly preferred S-alkyl-N,N-dialkylthiocarbamates employed herein include many known herbicides which have already received government approval for use with growing food crops, especially soybeans. Preferred among these thiocarbamate compounds are those wherein the alkyl groups are each in the range of $C_2$-$C_4$.

Compositions of the present type include those wherein the polymer matrix is a member selected from the group consisting of the commercially available cellulose acetate butyrates and the cellulose acetate propionates.

By proceeding in the manner of this invention, effective herbicidal compositions which comprise from about 25% to about 70% by weight of the herbicide are provided. It will be appreciated by those skilled in the art that such high levels of herbicide are particularly advantageous for field use. The compositions herein are especially useful for controlling weeds by applying said compositions to weed seeds at about the time of germination.

What is claimed is:

1. A sustained release herbicide composition comprising a solid solution or dispersion of from about 25% to about 70% by weight of substantially unpolymerized or undecomposed S-propyl dipropylthiocarbamate in an otherwise substantially dry, water-insoluble thermoplastic polymer matrix which is a member selected from the group consisting of cellulose acetate butyrate having a degree of acylation in the range from about 1.8 to about 2.7 and containing from about 10% to about 35% by weight of butyrate substituents and polypropylene having a flow point below the decomposition/polymerization temperature of S-propyl dipropylthiocarbamate.

2. A composition according to claim 1 comprising from about 25% to about 70% by weight of S-propyl dipropylthiocarbamate and a polymer matrix comprising cellulose acetate-butyrate.

3. A composition according to claim 2 in the form of particles whose smallest dimension is in the range of from about 0.5 mm. to about 1 mm.

4. A particulate composition according to claim 1 wherein the herbicide is S-propyl dipropylthiocarbamate, wherein the polymer matrix comprises said thermoplastic polypropylene, and wherein the smallest dimension of the particle is in the range of from about 0.5 mm. to about 1 mm.

5. A process for controlling weeds comprising applying to weed seeds to about the time of germination a composition according to claim 1.

* * * * *